(12) United States Patent
Mrochen et al.

(10) Patent No.: US 8,936,591 B2
(45) Date of Patent: Jan. 20, 2015

(54) APPARATUS FOR THE CROSS-LINKING OF OCULAR TISSUE WITH ELECTROMAGNETIC RADIATION

(75) Inventors: Michael Mrochen, Eglisau (CH); Theo Seiler, Zürich (CH)

(73) Assignee: Iroc Innocross AG, Zug (CH)

( * ) Notice: Subject to any disclaimer, the term of this patent is extended or adjusted under 35 U.S.C. 154(b) by 671 days.

(21) Appl. No.: 13/091,755

(22) Filed: Apr. 21, 2011

(65) Prior Publication Data
US 2011/0264082 A1 Oct. 27, 2011

(30) Foreign Application Priority Data
Apr. 21, 2010 (EP) .................... 10004224

(51) Int. Cl.
| A61B 18/18 | (2006.01) |
| A61N 5/06 | (2006.01) |
| A61F 9/008 | (2006.01) |
| A61B 18/20 | (2006.01) |
| A61B 18/00 | (2006.01) |
| A61F 9/007 | (2006.01) |

(52) U.S. Cl.
CPC .......... *A61F 9/008* (2013.01); *A61N 5/062* (2013.01); *A61B 18/203* (2013.01); *A61B 2018/00452* (2013.01); *A61F 2009/00872* (2013.01); *A61N 5/0616* (2013.01); *A61N 2005/0661* (2013.01); *A61F 9/0079* (2013.01); *A61F 2009/00851* (2013.01)
USPC ....................... 606/4; 606/5; 607/88

(58) Field of Classification Search
CPC .............. A61F 2009/007; A61F 2009/008; A61F 2009/00861; A61F 2009/00872; A61F 9/007; A61F 9/008; A61F 9/00821; A61F 9/00825; A61F 9/00827
USPC ........................... 606/4–6, 10–12; 607/88–93
See application file for complete search history.

(56) References Cited

U.S. PATENT DOCUMENTS 6,004,314 A * 12/1999 Wei et al. .................... 606/12
2007/0142828 A1 * 6/2007 Peyman ....................... 606/12

FOREIGN PATENT DOCUMENTS

| DE | 10 2006 030 219 | 1/2008 |
| DE | 20 2009 015 776 | 5/2010 |
| EP | 1 561 440 | 8/2005 |
| EP | 1 790 383 | 5/2007 |
| EP | 1 854 438 | 11/2007 |
| WO | WO 2007/028581 | 3/2007 |
| WO | WO 2008/000478 | 1/2008 |
| WO | WO 2008/008914 | 1/2008 |

OTHER PUBLICATIONS

European Search Report for European Application No. 10004224.1-2305, mailed Sep. 29, 2010 (7 pgs.).

* cited by examiner

*Primary Examiner* — Ahmed Farah
(74) *Attorney, Agent, or Firm* — John C. Pokotylo; Straub & Pokotylo

(57) ABSTRACT

An apparatus for generating an alteration of biomechanical properties of ocular tissue, into which a photosensitizer (14) has been introduced, contains means (18, 20) for radiating into the tissue electromagnetic radiation (12') which reacts with the photosensitizer for the purpose of generating a cross-linking. The setting means permit an inhomogeneous distribution of the irradiance in the tissue and a setting of the depth of action (16').

20 Claims, 2 Drawing Sheets

APPARATUS FOR THE CROSS-LINKING OF OCULAR TISSUE WITH ELECTROMAGNETIC RADIATION

Figure 1:
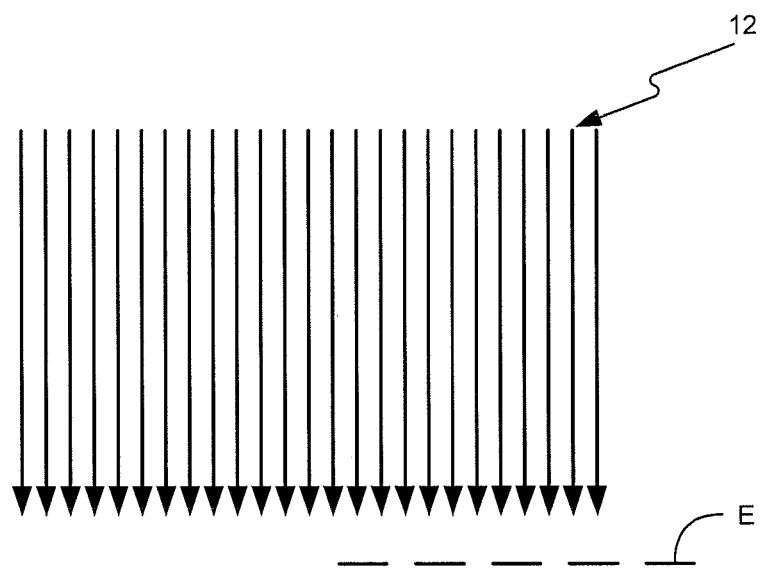
Figure 1:
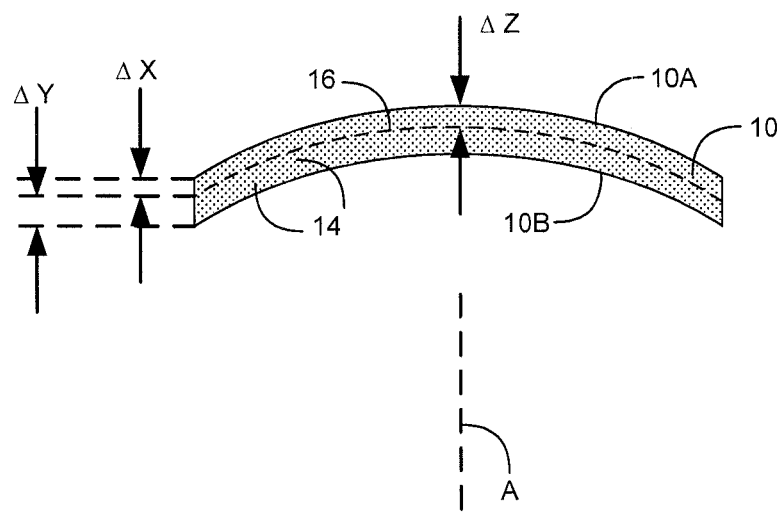

The invention relates to an apparatus for the cross-linking of ocular tissue with electromagnetic radiation, in particular UV radiation, whereby as a result of the cross-linking by means of a photosensitiser introduced into the ocular tissue the biomechanical properties of the ocular tissue are altered, with means for radiating the electromagnetic radiation into the tissue, whereby the radiated electromagnetic radiation activates the photosensitiser for a cross-linking.

The human eyeball is bounded by the outer tunic of the eyeball. By virtue of the intraocular pressure, the collagen-containing outer tunic of the eyeball is tightened and imparts an approximately spherical shape to the healthy eyeball. In the posterior region of the eyeball the outer tunic of the eyeball consists of the white sclera. Located in the anterior region is the cornea, which is transparent to visible light.

Deformations of the outer tunic of the eyeball may be the cause of defective vision. For example, one form of short-sightedness, axial myopia, may be the consequence of a scleral increase in the length of the eyeball. A surface of the cornea shaped as an ellipsoid may result in a form of astigmatism that is also designated as corneal distortion. Another disease of the cornea is designated as keratoconus. In the case of keratoconus, a progressive thinning and a conical deformation of the cornea of the eye occur as a consequence of a pathological softening of the cornea. With the increasing bulging, the cornea becomes thinner below the centre. It may rupture and form a scar. This permanently reduces visual acuity. The causes of keratoconus are largely unknown even today. It occurs with increased frequency within a family, which, inter alia, permits a genetic predisposition to be inferred. Atopic disorders such as allergic diseases constitute a further risk factor for the genesis of a keratoconus.

The conventional therapy for an advanced keratoconus provides for removing the diseased cornea and replacing it with an allogeneic graft. Such an operation is, however, an organ transplant, with the associated risks and complications. An appropriate visual faculty is frequently obtained only about two years after the operation. In addition, the transplantation of the cornea in the case of keratoconus mostly affects young persons, for which reason the transplant has to function perfectly over a period of decades.

In contrast to this, an improved therapy for keratoconus stabilises the cornea by cross-linking. The treatment permits a photochemical, non-tissue-resecting stabilisation or change of the biomechanical and biochemical properties of the cornea. The therapeutic principle is also applicable to other affected regions of the eye. A photosensitiser solution is introduced into the eye tissue to be changed and is exposed to a primary radiation. Electromagnetic radiation within the wavelength range from approximately 300 nm to 800 nm (UV-A radiation or visible light) is employed as primary radiation.

Appropriate apparatuses for treating the outer tunic of the eyeball are known from printed publications WO 2007/128581 A2 and WO 2008/000478 A1.

EP 1 561 440 B1 describes an apparatus in which, with a relatively complex structural design, a homogeneous distribution of the radiation is generated within the ocular tissue. Therein a moulding is mounted onto the cornea, in order to bring the latter into a desired shape while the ocular tissue is altered with regard to its strength by means of electromagnetic radiation and the photosensitiser. Such a moulding may also be employed in connection with the present invention.

An apparatus according to WO 2007/128581 A2 serves for strengthening the sclera located in the posterior portion of the eye. In this case the primary radiation can act on the sclera through the interior of the eye or through pads resting against it from outside. By means of a photomediator or photosensitiser a cross-linking is brought about in the sclera. As a result, a growth of the sclera is counteracted and a progression of the axial myopia is prevented.

EP 1 854 438 A1 describes an ophthalmological apparatus for preventing myopia, with which the sclera is strengthened by means of a photosensitiser.

Printed publication WO 2008/000478 A1 describes an irradiation system for biomechanical stabilisation of the cornea. Here too, in conjunction with a photosensitiser a cross-linking in respect of the cornea can be brought about. The irradiation system offers the possibility of treating specific diseases such as keratoconus.

The alteration of the form and/or of mechanical properties of eye tissue, in particular of the cornea and generally of the sclera, by means of an introduced photosensitiser and electromagnetic radiation is well-known as such in the state of the art, in particular as mentioned above. With regard to the chemical composition of the photosensitiser, reference is made to the state of the art, also with regard to the type of electromagnetic radiation employed, in particular the suitable wavelengths in conjunction with certain photosensitisers.

However, complex dependences conflict with a routine use of cross-linking therapy on the eye tissue. The relationships between the doses employed and the effect thereof in the eye tissue are highly diverse. By way of dose in this sense there enter into consideration, in particular, the electromagnetic radiation with regard to its intensity as well as its distribution in space and time; the photosensitiser employed with regard to its chemical structure, concentration, and action in space and time. The effects of different doses of these parameters on and in the eye tissue of a patient are very highly dependent on properties (measurement data) with respect to the patient. In this connection it is to be taken into consideration, in particular, that the effect of the cross-linking implemented with the radiation and the photosensitiser may also be undesirable and may extend so far as to damage the eye tissue or harm the functioning of the eye.

The object underlying the invention is to make available an apparatus of the type stated in the introduction, with which the biomechanical properties of ocular tissue can be altered selectively and precisely.

To this end, the invention makes available an apparatus for generating an alteration of biomechanical properties of ocular tissue that contains photosensitiser, with means for radiating into the tissue electromagnetic radiation that brings about a cross-linking with the photosensitiser, characterised by means for setting an inhomogeneous distribution of the irradiance of the electromagnetic radiation in the ocular tissue.

According to a preferred configuration of the invention, the stated ocular tissue is the cornea of the eye.

Another preferred configuration of the invention provides that the stated electromagnetic radiation is radiated into the cornea over its entire surface, i.e. the irradiation of the cornea takes place substantially over the entire ophthalmologically relevant anterior surface thereof. This enables a simple application and introduction of the photosensitiser into the ocular tissue, and also a simple configuration of the optical means for the radiating of the electromagnetic radiation.

Given use of the known photosensitisers, in the case of the electromagnetic radiation it is normally a question of UV radiation, and this is also the case here.

Depending upon the medical indication, the invention enables an inhomogeneous distribution of the electromagnetic radiation and, as a result, also a desired distribution of the cross-linking and also of the accompanying alterations in the biomechanical properties of the ocular tissue. Hence an alteration of the shape of the irradiated ocular tissue can be obtained selectively and precisely, since, depending on the respective local biomechanical properties, the intraocular pressure has a variable effect with respect to the shape of the tissue. More strongly cross-linked regions of the tissue, i.e. more strongly 'hardened' regions, display a slighter bulging in comparison with softer tissue regions.

The invention also enables a consideration and compensation of the angles between the radiating direction of the electromagnetic radiation and the surface of the ocular tissue—that is to say, in particular of the cornea. In this connection the invention takes into consideration the fact that, depending on the place of impingement on the surface of the tissue, the electromagnetic radiation firstly is reflected variably in location-dependent manner (depending on the angle of incidence) and secondly has a variable irradiance. For example, the radiation is reflected more strongly in outer regions of the cornea situated further away from the optical axis of the system (that is to say, in regions that are also further away from the visual axis of the eye) by reason of the flatter angle of incidence than in central regions of the cornea, having the consequence that the radiation in the outer regions of the tissue, further away from the axis—in comparison with regions situated closer to the axis—not only penetrates into the tissue to a lesser extent but also activates the photosensitiser there with a lower effective irradiance. According to the invention, this is taken into account selectively by the irradiance being set inhomogeneously in such a way that, for example, the cross-linking takes place everywhere, if this is desired, homogeneously over the entire irradiated ocular tissue.

The term "irradiance" here is to be understood, without exception, in such a way that it is measured in a plane that is perpendicular to the optical axis of the means for setting the distribution of the irradiance. Irradiance is conventionally measured in watts per square meter.

The fixing, performed here, of the irradiance and of its distribution with respect to a plane E that is perpendicular to the optical axis A has the advantage that the desired distribution of the irradiance can be effected, both locally and with regard to intensity, with relatively simple optical means. With this, an alteration of the desired irradiance distribution in a given system is also possible relatively easily, by, for example, either the optical component being exchanged or the optical component being chosen in such a way that it can be altered. Such a simple alteration is possible, in particular, in the case where use is made of an optical element in the form of a liquid-crystal plate, in the form of a lens with liquid wetting, or even simply with adjustable polarising filters.

Another preferred configuration of the invention provides that the stated means for setting an inhomogeneous radiation-density distribution enable an alteration of the inhomogeneity of the distribution. In other words: an apparatus is made available that enables the ophthalmologist to bring about, depending upon the indication, an alteration in the radial and/or meridional radiation-density distribution without great effort and with one and the same apparatus, only by alteration of the optical means or of the setting of the given optical means.

Preferably, by way of optical element for setting the irradiance distribution of the electromagnetic radiation there is optionally employed: an absorbing optical element (neutral density filter), a refracting optical element, a diffracting optical element, a deformable mirror, an electrowetting lens, a micromirror array, polarising filters, or a liquid-crystal plate.

Another preferred configuration of the invention provides that the means for setting the electromagnetic radiation-density distribution are designed in such a way that only a part of the ocular tissue, in particular only a part of the cornea, is exposed to electromagnetic radiation. This is to be understood not only in the transverse direction (perpendicular to the optical axis) but, in particular, also in the direction of the radiation—that is to say, in the sense of the depth of action of the electromagnetic radiation in the tissue. For instance, there may be provision to set the electromagnetic radiation with the stated means in such a way that only an outer part of the cornea is exposed to electromagnetic radiation as far as a certain predetermined depth of action. For this purpose the intensity of the radiation is set accordingly, so that the radiation is substantially completely absorbed (by the photosensitisers or by other absorbing parts in the tissue) as far as the desired depth of action. The radiation density is accordingly capable of being set (chosen) radially and/or meridionally.

The invention will be elucidated in more detail in the following on the basis of an exemplary embodiment.

Figure 2:
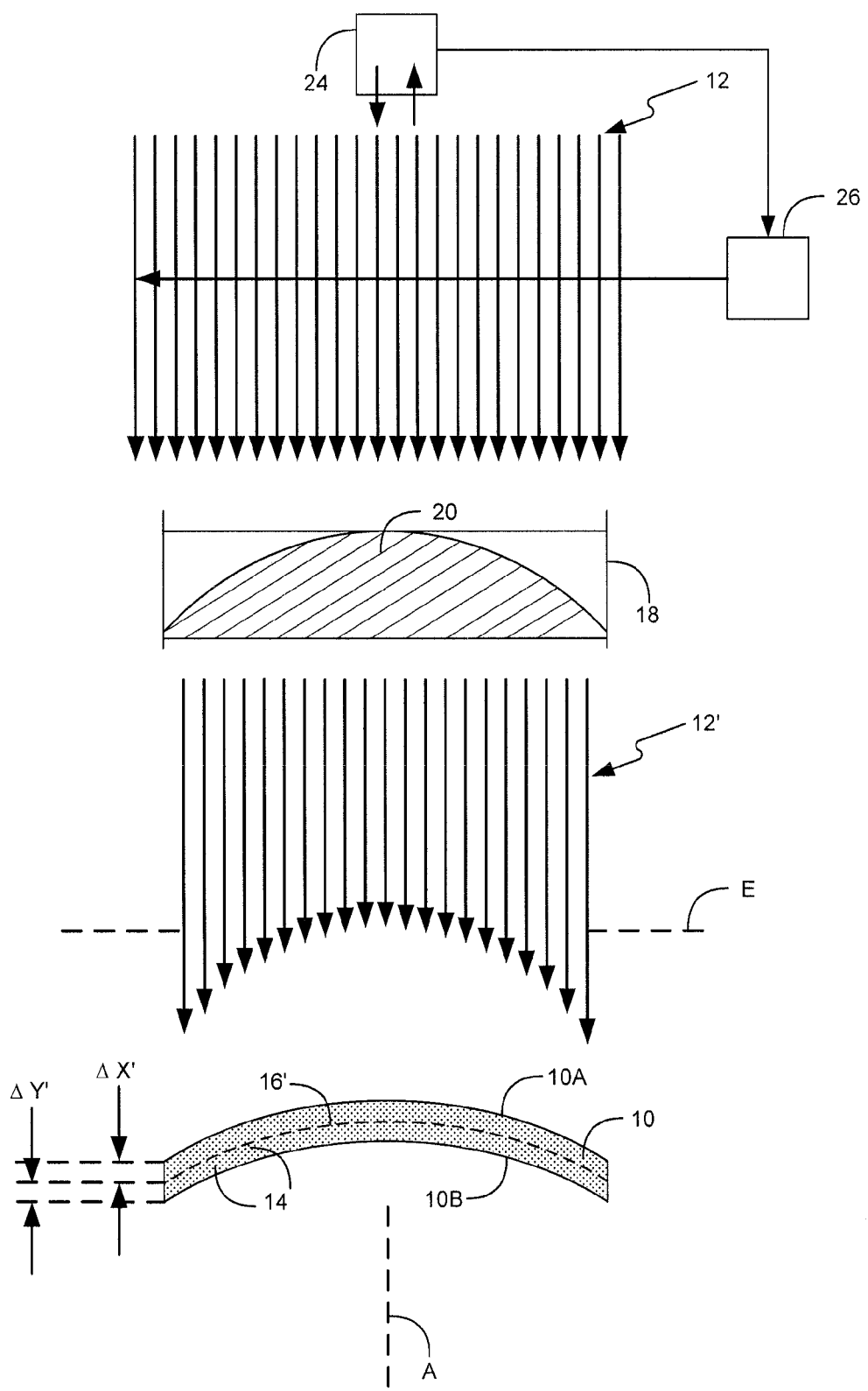

Shown are:

FIG. 1 schematically, the interaction between electromagnetic radiation and a cornea provided with a photosensitiser; and FIG. 2 an apparatus for generating an alteration of the biomechanical properties, on the basis of an example constituted by a cornea that contains a photosensitiser.

In the schematic representation according to FIG. 1 a cornea 10 is irradiated over its entire surface, i.e. over its extent from limbus to limbus, with electromagnetic UV radiation 12 (in the case of certain known photosensitisers, UVA radiation also comes into operation). The cornea 10 is permeated homogeneously in known manner by a previously introduced photosensitiser 14. Photosensitisers as such are known in the state of the art, for example riboflavin. After being dripped onto the cornea, the photosensitiser distributes itself substantially uniformly within the entire cornea. By virtue of the irradiation with electromagnetic beams, biochemical and biomechanical processes are induced, in particular cross-linking—that is to say, a process that results in a strengthening of the cornea, that is to say, an alteration of the biomechanical properties of the cornea. Photosensitisers, as substances occurring naturally in the body, are subsequently decomposed in residue-free manner within relatively short periods of time. The electromagnetic radiation within the UV range that is employed here is not to be confused or compared, with regard to its intensity and effect, with electromagnetic radiation that is employed for an ablation of the cornea, for example in the case of LASIK or keratoplasty.

The intensity of the electromagnetic radiation 12 is ordinarily set as low as possible with a view to conserving the tissue. In FIG. 1 the depth of penetration of the electromagnetic radiation—that is to say, its so-called depth of action—is indicated by the dashed line 16. At the line 16 the electromagnetic radiation 12 radiated into the cornea 10 is accordingly substantially absorbed and subsequently—i.e. in deeper regions of the cornea close to the back 10b thereof—no longer has any effect. The front of the cornea is denoted in the Figures by 10a.

As FIG. 1 shows, the depth of action, indicated by the line 16, of the electromagnetic radiation with regard to the activation of the photosensitiser is dependent on the location of the radiating into the cornea 10. The depth of action decreases radially outwards, starting from an ocular axis A. In the exemplary embodiment represented in FIG. 1 the intensity of the radiated radiation 12—more precisely, the irradiance—in a plane E which is perpendicular to the ocular axis A is homogeneous—i.e. constant in the plane E. The present invention is based on the perception that, despite the homogeneous distribution of the radiance in the plane E, the depth of action of the radiation in the corneal tissue 10 containing the photosensitiser decreases radially outwards—i.e. decreases with increasing distance from the ocular axis A. Whereas the depth of action $\Delta z$ of the radiation in the region of the ocular axis A in the exemplary embodiment that is represented reaches, by reason of the intensity of the electromagnetic radiation 12, approximately as far as the middle of the corneal thickness, the depth of action $\Delta x$ at the peripheral edge of the cornea 10 is distinctly slighter, and correspondingly the region $\Delta y$ in which the electromagnetic radiation achieves no significant effect with the photosensitiser is distinctly greater than half the thickness of the cornea.

The invention is based on the perception of these relationships, which are explained as follows:

The effect of the radiation in the corneal tissue depends on the local irradiance (typical symbol 'E', defined as the power of the incoming electromagnetic energy per unit area). In the situation represented in FIG. 1 the irradiance depends substantially on two effects: on the one hand, on the angle between the radiation and the surface 10a of the cornea 10, and, on the other hand, on the reflection of radiation on the surface 10a. By reason of the given relative angles between the radiating direction of the radiation and the surface 10a of the cornea, more and more radiation is reflected, starting from the central ocular axis A, radially outwards to the periphery of the cornea (because, starting from the middle, the angle becomes more and more acute from, initially, approximately 90°). On the other hand, the irradiance radially outwards also becomes smaller and smaller by reason of the angle between the tissue and the incident radiation. In addition to this aspect, the depth of action in the peripheral direction is reduced even more greatly, because the relationship between radiation intensity and depth of action or degree of cross-linking is non-linear. These effects are additive and result in the diminution, represented in FIG. 1, of the depth of action 16 of the radiation with increasing radial distance from the ocular axis A.

The term "ocular axis" is defined variably in ophthalmology. In connection with the present invention, the definition of the "axis" that is drawn upon is not exactly what matters. By the term "axis" here, for example, the optical axis of the optical system constituted by the eye may be imagined—that is to say, a straight line that connects the centres of curvature of the refracting faces in a centred system. In the case of arrangements represented in the Figures, the optical axis of the eye also coincides with the optical axis of the optical system applying the radiation. In the context of this description, the term "radially" relates to the distance from the axis A in the direction perpendicular thereto, and the term "axially" relates to a direction parallel to the axis A. The plane E accordingly runs radially.

FIG. 2 shows a further apparatus for generating an alteration of the biomechanical properties of ocular tissue, here in the form of a cornea 10. The electromagnetic radiate 12 passes, prior to its impingement on the cornea 10, through means 18, 20 with which the depth of action of the electromagnetic radiation in the ocular tissue can be set. In FIG. 2 the irradiance of the electromagnetic radiation 12 is represented by the length of the arrows. The electromagnetic radiation 12 is generated by a known source of radiation (not represented). The means 18, 20 for setting the irradiance distribution exhibit a housing 18 in which, in the exemplary embodiment that is represented, a radiation-absorber 20 (neutral density filter) is optionally arranged. The absorption plate is only represented schematically in FIG. 2. It exclusively absorbs the radiation without bringing about imaging properties—that is to say, in particular, without generating a change in direction from the incident radiation to the emergent radiation. The hatching in the element 20 according to FIG. 2 corresponds to the absorbing thickness of the element, which decreases radially outwards.

After passing through the element 20, the electromagnetic radiation has the irradiance distribution 12', in which the length of the arrows represents the local irradiance schematically in each instance. With this irradiance distribution, in which the irradiance increases radially with its distance from the axis A, a depth of action with respect to the activation of the photosensitiser 14 in the cornea 10 according to the line 16' is obtained. In the exemplary embodiment that is represented, it is being endeavored to obtain a depth of action corresponding to the line 16' over the entire radial extent of the cornea 10 substantially in the middle of the axial extent of the cornea. Correspondingly, the depth of action $\Delta x'$ measured in the axial direction is approximately equal to the thickness $\Delta y'$ of the region of the cornea in which no significant alteration of the biomechanical properties of the cornea takes place.

The depth of action of the electromagnetic radiation and of the associated cross-linking of the tissue can be determined by optical coherence tomography. It will be understood that the representations and descriptions of FIGS. 1 and 2 are rotationally symmetrical about the axis A, i.e. the sections that are represented are valid schematically for each direction of a section that is perpendicular to the axis A and that also includes the axis A. The apparatus according to the invention is accordingly set up in such a way that the inhomogeneity (needed for the respective medical indication) of the electromagnetic radiation is capable of being set meridionally and radially.

By way of means 20 for setting the irradiance distribution of the electromagnetic radiation 12', besides the radiation-absorber described above in exemplary manner there enter into consideration: a refracting optical element, a diffracting optical element, a deformable mirror, an electrowetting lens, a micromirror array, polarising filters, or a liquid-crystal plate or a combination of one or more of these elements.

With the invention it is possible to bring about an alteration of the eye tissue with respect to its form and/or at least one mechanical property, whereby with at least one optical element 20 a light distribution is generated in the tissue that results in an initially defined distribution of the cross-linkages deep within the tissue structures. The local (geometrical) distribution of the cross-linkings is in this case controlled by using the element 20 or several elements at this point optionally radially, axially and/or meridionally in relation to the anterior surface 10a or the posterior surface 10b of the cornea 10. The light distribution (irradiance distribution) is, in particular, controlled in such a way that projection effects and reflection losses of the radiation are taken into consideration. The invention accordingly enables, by variation of the radiation intensity and/or radiation dose, a selective reshaping of the cornea in the interplay between the biomechanical properties of the cornea and the intraocular pressure.

FIG. 2 also shows a further development of the inventive idea, with the inclusion of means 24 for determining the current depth of action in the tissue, for example in the cornea 10, generated during the radiating of electromagnetic radiation. For example, an instrument, known as such, pertaining to optical coherence tomography (OCT) is suitable by way of means for determining the depth of action. Such an OCT device is denoted schematically in FIG. 2 by reference symbol 24. Means 26 are provided in order to control the electromagnetic radiation in space and time. Such means for controlling electromagnetic radiation in space and time are also widely known in ophthalmological technology.

With the means 24 for optical coherence tomography, during the radiating of electromagnetic radiation 12 the depth of action 16' obtained in the given case is determined 'online', and in accordance with the determined depth of action and a comparison with a specified depth the device 26 for controlling the electromagnetic radiation 12 can then be driven in order to obtain a desired final depth of action.

The final depth of action to be achieved for a patient may, for example, be acquired empirically, depending on the diagnosis and on empirical or estimated data for the therapy to be striven for by means of alteration of the biomechanical properties of the tissue. For example, the depth of action can be determined empirically by means of a plurality of pig eyes which are provided with the chosen photosensitiser and in which the irradiance is varied within the scope of a series of tests and whereby the depth of action is then measured in each instance by means of coherence tomography. The term "depth of action" designates the segment in which, starting from the anterior surface of the cornea, the biomechanical properties of the tissue have been altered in comparison with the initial state by the interaction of the photosensitiser with the radiation. Hence a so-called profile for the depth of action arises, i.e. a function of the depth of action depending on the location in the tissue. In the schematic exemplary embodiment according to FIG. 2, the final depth of action 16' is uniform approximately in the middle of the cornea, as described above. But with certain indications it may be desired to obtain a non-uniform final depth of action, in such a manner that it does not have the uniform progression, shown schematically in FIG. 2, in the middle of the cornea but varies as a function of the distance from the central axis A, for example in such a way that, depending upon the indication, in the middle or peripherally the final depth of action runs more closely or further along the front 10a or the rear 10b of the cornea.

The final depth of action may, for example, depending upon diagnosis and indication, be ascertained empirically using the so-called topographic data (surveying of the surface 10a of the cornea), the corneal thickness, and with the aid of wavefront measurements.

The invention claimed is:

1. Apparatus for generating an alteration of biomechanical properties of a cornea (10) that contains photosensitizer (14), further comprising means for radiating into the cornea (10) electromagnetic radiation (12') which with the photosensitizer (14) brings about a cross-linking, wherein the means (18, 20) for radiating set a depth of action (16, 16') of the electromagnetic radiation (12') in the cornea (10) in such a manner that, starting from the anterior surface (10a) of the cornea (10), in the direction of the radiation as far as a predetermined depth of action (16, 16') an outer part of the cornea is exposed to electromagnetic radiation which is partially absorbed as far as the predetermined depth of action, whereas in deeper regions of the cornea close to the back (10b) thereof the electromagnetic radiation has no effect, wherein the depth of action is the depth of penetration of the electromagnetic radiation into the cornea.

2. Apparatus according to claim 1, wherein said means (18, 20) for radiating set the depth of action (16') of the electromagnetic radiation radially.

3. Apparatus according to claim 2, further comprising means (24) for determining the depth of action (16') achieved in the course of radiating the electromagnetic radiation (12') during the radiating of the electromagnetic radiation.

4. Apparatus according to claim 2, wherein the means (18, 20) for radiating have been set up to radiate the electromagnetic radiation into the ocular tissue with a higher irradiance in regions further away from their central axis than in regions situated closer to the axis (A).

5. Apparatus according to claim 2, wherein the means (18, 20) for radiating radiate the electromagnetic radiation into the ocular tissue (10) with a lower irradiance in regions further away from their central axis than in regions situated closer to the axis (A).

6. Apparatus according to claim 1, wherein said means (18, 20) for radiating set the depth of action (16') of the electromagnetic radiation meridionally.

7. Apparatus according to claim 6, further comprising means (24) for determining the depth of action (16') achieved in the course of radiating the electromagnetic radiation (12') during the radiating of the electromagnetic radiation.

8. Apparatus according to claim 6, wherein the means (18, 20) for radiating radiate the electromagnetic radiation into the ocular tissue with a higher irradiance in regions further away from their central axis than in regions situated closer to the axis (A).

9. Apparatus according to claim 6, wherein the means (18, 20) for radiating radiate the electromagnetic radiation into the ocular tissue (10) with a lower irradiance in regions further away from their central axis than in regions situated closer to the axis (A).

10. Apparatus according to claim 1, further comprising means (24) for determining the depth of action (16') achieved in the course of radiating the electromagnetic radiation (12') during the radiating of the electromagnetic radiation.

11. Apparatus according to claim 10, further comprising means (26) for controlling, during the radiating of the electromagnetic radiation, the electromagnetic radiation in a manner depending on the determined depth of action.

12. Apparatus according to claim 11, wherein the means (26) for controlling the electromagnetic radiation in a manner depending on the determined depth of action exhibit an instrument for optical coherence tomography.

13. Apparatus according to claim 11, wherein the means (26) for controlling the electromagnetic radiation in a manner depending on the determined depth of action exhibit an instrument for optical coherence tomography.

14. Apparatus according to claim 10, wherein the means (18, 20) for radiating radiate the electromagnetic radiation into the ocular tissue with a higher irradiance in regions further away from their central axis than in regions situated closer to the axis (A).

15. Apparatus according to claim 10, wherein the means (18, 20) for radiating radiate the electromagnetic radiation into the ocular tissue (10) with a lower irradiance in regions further away from their central axis than in regions situated closer to the axis (A).

16. Apparatus according to claim 10, wherein the means (26) for controlling the electromagnetic radiation in a manner depending on the determined depth of action exhibit an instrument (18,20) for optical triangulation.

17. Apparatus according to claim 10, wherein the means (26) for controlling the electromagnetic radiation in a manner depending on the determined depth of action exhibit a Scheimpflug camera.

18. Apparatus according to claim 1, wherein the means (18, 20) for radiating radiate the electromagnetic radiation into the ocular tissue with a higher irradiance in regions further away from their central axis than in regions situated closer to the axis (A).

19. Apparatus according to claim 1 wherein the means (18, 20) for radiating radiate the electromagnetic radiation into the ocular tissue (10) with a lower irradiance in regions further away from their central axis than in regions situated closer to the axis (A).

20. Apparatus for generating an alteration of biomechanical properties of a cornea (10) that contains photosensitizer (14), further comprising means for radiating into the cornea (10) electromagnetic radiation (12') which with the photosensitizer (14) brings about a cross-linking, wherein the means (18, 20) for radiating set a depth of action (16, 16') of the electromagnetic radiation (12') in the cornea (10) in such a manner that, starting from the anterior surface (10a) of the cornea (10), in the direction of the radiation as far as a predetermined depth of action (16, 16') an outer part of the cornea is exposed to electromagnetic radiation, at least some of which is absorbed as far as the predetermined depth of action, whereas in deeper regions of the cornea close to the back (10b) thereof the electromagnetic radiation has no effect.

\* \* \* \* \*